United States Patent
Nadir et al.

(10) Patent No.: US 10,105,410 B2
(45) Date of Patent: Oct. 23, 2018

(54) HEPARANASE INHIBITORY PEPTIDES AND USE THEREOF FOR TREATING CLINICAL PATHOLOGIES

(71) Applicant: RAMBAM MED-TECH LTD., Haifa (IL)

(72) Inventors: Yona Nadir, Zichron Yaakovv (IL); Benjamin Brenner, Haifa (IL)

(73) Assignee: RAMBAM MED-TECH LTD., Haifa (IL)

( * ) Notice: Subject to any disclaimer, the term of this patent is extended or adjusted under 35 U.S.C. 154(b) by 0 days.

(21) Appl. No.: 15/125,340

(22) PCT Filed: Mar. 9, 2015

(86) PCT No.: PCT/IL2015/050246
§ 371 (c)(1),
(2) Date: Sep. 12, 2016

(87) PCT Pub. No.: WO2015/136527
PCT Pub. Date: Sep. 17, 2015

(65) Prior Publication Data
US 2017/0202900 A1 Jul. 20, 2017

Related U.S. Application Data

(60) Provisional application No. 61/950,235, filed on Mar. 10, 2014.

(51) Int. Cl.
*A61K 38/18* (2006.01)
*A61P 15/00* (2006.01)
*A61K 38/00* (2006.01)

(52) U.S. Cl.
CPC .................. *A61K 38/005* (2013.01)

(58) Field of Classification Search
None
See application file for complete search history.

(56) References Cited

FOREIGN PATENT DOCUMENTS

| WO | 9325221 A1 | 12/1993 |
|---|---|---|
| WO | 9417784 A1 | 8/1994 |
| WO | 2012098542 A2 | 7/2012 |

OTHER PUBLICATIONS

Park et al., "Measuring Response in Solid Tumors: Comparison of RECIST and WHO Response Criteria," Jpn. J. Clin. Oncol. 33: 533-537 (2003).*
Chand et al., "Structure, function and biology of tissue factor pathway inhibitor-2," Thromb. Haemost. 94:1122-1130 (2005).*
Axelman, E., et la., "Novel peptides that inhibit heparanase activation of the coagulation system", Thrombosis and Haemostasis, Sep. 2014, pp. 466-477, vol. 112, Issue: 3.
Sprecher, C.A., et al., "Molecular cloning, expression, and partial characterization of a second human tissue-factor-pathway inhibitor", Proceedings of the National Academy of Sciences, Apr. 1994, pp. 3353-3357, vol. 91, Issue: 8, USA.

* cited by examiner

*Primary Examiner* — Julie Ha
*Assistant Examiner* — Kristina M Hellman
(74) *Attorney, Agent, or Firm* — The Roy Gross Law Firm, LLC; Roy Gross

(57) ABSTRACT

The present invention is directed to peptides derived from certain domains of tissue factor pathway inhibitor (TFPI) for use in the treatment of solid tumors and diseases or disorders associated with abnormal clotting.

4 Claims, 15 Drawing Sheets

Specification includes a Sequence Listing.

| Seq ID No: | Amino acid sequence |
|---|---|
| 3, 8 | 35 ICLLPLDYGPCRAL 48 |
| 4, 8 | 33 AEICLLPLDYGPCR 46 |
| 5, 8 | 31 NNAEICLLPLDYGP 44 |
| 7, 9 | 72 NANNFYTWEAC 82 |
| 2, 9 | 74 NNFYTWEACDDACW 87 |

Back        Front

Fig. 7A  Fig. 7B

SEQUENCE LISTING

```
<160> NUMBER OF SEQ ID NOS: 9

<210> SEQ ID NO 1
<211> LENGTH: 14
<212> TYPE: PRT
<213> ORGANISM: artificial sequence
<220> FEATURE:
<223> OTHER INFORMATION: peptide

<400> SEQUENCE: 1
```

```
Leu Leu Arg Tyr Tyr Tyr Asp Arg Tyr Thr Gln Ser Cys Arg
1               5                   10

<210> SEQ ID NO 2
<211> LENGTH: 14
<212> TYPE: PRT
<213> ORGANISM: artificial sequence
<220> FEATURE:
<223> OTHER INFORMATION: peptide

<400> SEQUENCE: 2

Asn Asn Phe Tyr Thr Trp Glu Ala Cys Asp Asp Ala Cys Trp
1               5                   10

<210> SEQ ID NO 3
<211> LENGTH: 14
<212> TYPE: PRT
<213> ORGANISM: artificial sequence
<220> FEATURE:
<223> OTHER INFORMATION: peptide

<400> SEQUENCE: 3

Ile Cys Leu Leu Pro Leu Asp Tyr Gly Pro Cys Arg Ala Leu
1               5                   10

<210> SEQ ID NO 4
<211> LENGTH: 14
<212> TYPE: PRT
<213> ORGANISM: artificial sequence
<220> FEATURE:
<223> OTHER INFORMATION: peptide

<400> SEQUENCE: 4

Ala Glu Ile Cys Leu Leu Pro Leu Asp Tyr Gly Pro Cys Arg
1               5                   10

<210> SEQ ID NO 5
<211> LENGTH: 14
<212> TYPE: PRT
<213> ORGANISM: artificial sequence
<220> FEATURE:
<223> OTHER INFORMATION: peptide

<400> SEQUENCE: 5

Asn Asn Ala Glu Ile Cys Leu Leu Pro Leu Asp Tyr Gly Pro
1               5                   10

<210> SEQ ID NO 6
<211> LENGTH: 14
<212> TYPE: PRT
<213> ORGANISM: artificial sequence
<220> FEATURE:
<223> OTHER INFORMATION: peptide

<400> SEQUENCE: 6

Arg Tyr Tyr Tyr Asp Arg Tyr Thr Gln Ser Cys Arg Gln Phe
1               5                   10

<210> SEQ ID NO 7
<211> LENGTH: 11
<212> TYPE: PRT
<213> ORGANISM: artificial sequence
<220> FEATURE:
<223> OTHER INFORMATION: peptide

<400> SEQUENCE: 7
```

```
Asn Ala Asn Asn Phe Tyr Thr Trp Glu Ala Cys
1               5                   10

<210> SEQ ID NO 8
<211> LENGTH: 9
<212> TYPE: PRT
<213> ORGANISM: artificial sequence
<220> FEATURE:
<223> OTHER INFORMATION: peptide

<400> SEQUENCE: 8

Ile Cys Leu Leu Pro Asp Tyr Gly Pro
1               5

<210> SEQ ID NO 9
<211> LENGTH: 9
<212> TYPE: PRT
<213> ORGANISM: artificial sequence
<220> FEATURE:
<223> OTHER INFORMATION: peptide

<400> SEQUENCE: 9

Asn Asn Phe Tyr Thr Trp Glu Ala Cys
1               5
```

HEPARANASE INHIBITORY PEPTIDES AND USE THEREOF FOR TREATING CLINICAL PATHOLOGIES

RELATED APPLICATIONS

This application is a National Phase of PCT Patent Application No. PCT/IL2015/050246 having International filing date of Mar. 9, 2015, which claims the benefit of priority under 35 USC § 119(e) of U.S. Provisional Patent Application No. 61/950,235 filed on Mar. 10, 2014. The contents of the above applications are all incorporated by reference as if fully set forth herein in their entirety.

FIELD OF THE INVENTION

The present invention is directed to peptides derived from certain domains of Tissue Factor Pathway Inhibitor (TFPI) for use in the treatment of solid tumors and diseases or disorders associated with abnormal clotting.

BACKGROUND OF THE INVENTION

Heparanase, is an endo-p-D-glucuronidase capable of cleaving heparan sulfate (HS) side chains at a limited number of sites, yielding HS fragments of still appreciable size (5-7 kDa).

Expression of heparanase is restricted primarily to the placenta, platelets, keratinocytes, and activated cells of the immune system, with little or no expression in connective tissue cells and most normal epithelia. One of the prime physiological sources for heparanase is platelets.

Heparanase was recognized over the years as a pro-inflammatory and a pro-metastatic protein. It was also shown that heparanase may affect the hemostatic system in a non-enzymatic manner as it up-regulates the expression of the blood coagulation initiator—tissue factor (TF) and interact with tissue factor pathway inhibitor (TFPI) on cell surface. This activity is leading to dissociation of TFPI from the cell membrane of endothelial and tumor cells, resulting in increased cell surface coagulation activity.

Moreover, heparanase was shown to enhance TF activity resulting in increased factor Xa production and activation of the coagulation system. Heparanase was further shown to promote tumor angiogenesis in vivo.

WO2012/098542, of some of the inventors of the present invention, discloses peptides with proposed inhibitory activity to the TF/heparanase complex.

There remains an unmet need in the art for potent methods for preventing or attenuating coagulation, while not interfering with normal hemostasis, and for inhibiting the development of solid tumors.

SUMMARY OF THE INVENTION

The present invention is based in part on the unexpected discovery that peptides, 7 to 20 amino acids long, derived from the first or third Kunitz domain of tissue factor pathway inhibitor (TFPI), significantly attenuate or inhibit heparanase procoagulant activity, while not interfering with normal hemostasis. Furthermore, said peptides were shown to reduce tumor size, attenuate the rate of tumor development, improve survival, inhibit tumor relapse and reduce the rate of tumor relapse.

According to some embodiments, there is provided a method for treating a disease or disorder associated with abnormal clotting in a subject in need thereof comprising administering to the subject a therapeutic composition comprising at least one peptide derived from the first or third Kunitz domain of tissue factor pathway inhibitor.

According to some embodiments, said tissue factor pathway inhibitor is tissue factor pathway inhibitor-2 (TFPI-2).

According to some embodiments, said at least one peptide is consisting of 7-20 amino acids.

According to some embodiments, said at least one peptide is 10 to 15 amino acid long and comprising SEQ ID NO: 8. According to some embodiments, said at least one peptide further comprises Cysteine and Arginine at the C terminus of SEQ ID NO: 8. According to some embodiments, said at least one peptide further comprises Alanine and Glutamic Acid at the N terminus of SEQ ID NO: 8. According to some embodiments, said at least one peptide further comprises Cysteine and Arginine at the C terminus of SEQ ID NO: 8 and Alanine and Glutamic Acid at the N terminus of SEQ ID NO: 8.

According to some embodiments, said at least one peptide is 10 to 15 amino acid long and comprising SEQ ID NO: 9. According to some embodiments, said at least one peptide is 10 to 15 amino acid long and comprising SEQ ID NO: 9.

According to some embodiments, said at least one peptide comprises an amino acid sequences selected from SEQ ID NOs: 1 through 9. Each possibility represents a separate embodiment of the present invention.

According to some embodiments, said at least one peptide comprises an amino acid sequences selected from SEQ ID NOs: 8 through 9 and combinations thereof. According to some embodiments, said at least one peptide comprises an amino acid sequences selected from SEQ ID NOs: 2-5 and 7.

According to some embodiments, said at least one peptide comprises an amino acid sequences set forth in SEQ ID NOs: 8. According to some embodiments, said at least one peptide comprises an amino acid sequences selected from SEQ ID NOs: 3-5.

According to some embodiments, said at least one peptide comprises an amino acid sequences set forth in SEQ ID NOs: 9. According to some embodiments, said at least one peptide comprises an amino acid sequences selected from SEQ ID NOs: 2 and 7.

According to some embodiments, said at least one peptide comprises an amino acid sequences set forth in SEQ ID NO: 1 (LLRYYYDRYTQSCR).

According to some embodiments, said at least one peptide comprises an amino acid sequences set forth in SEQ ID NO: 2 (NNFYTWEACDDACW).

According to some embodiments, said at least one peptide comprises an amino acid sequences set forth in SEQ ID NO: 3 (ICLLPLDYGPCRAL).

According to some embodiments, said at least one peptide comprises an amino acid sequences set forth in SEQ ID NO: 4 (AEICLLPLDYGPCR).

According to some embodiments, said at least one peptide comprises an amino acid sequences set forth in SEQ ID NO: 5 (NNAEICLLPLDYGP).

According to some embodiments, said at least one peptide comprises an amino acid sequences set forth in SEQ ID NO: 6 (RYYYDRYTQSCRQF)

According to some embodiments, said at least one peptide comprises an amino acid sequences set forth in SEQ ID NO: 7 (NANNFYTWEAC).

According to some embodiments, said at least one peptide comprises the amino acid sequence set forth in SEQ ID NO: 8 (ICLLPLDYGP).

According to some embodiments, said at least one peptide comprises the amino acid sequence set forth in SEQ ID NO: 9 (NNFYTWEAC).

According to some embodiments, said at least one peptide is consisting of the amino acid sequences set forth in SEQ ID NO: 1 (LLRYYYDRYTQSCR).

According to some embodiments, said at least one peptide is consisting of the amino acid sequences set forth in SEQ ID NO: 2 (NNFYTWEACDDACW).

According to some embodiments, said at least one peptide is consisting of the amino acid sequences set forth in SEQ ID NO: 3 (ICLLPLDYGPCRAL).

According to some embodiments, said at least one peptide is consisting of the amino acid sequences set forth in SEQ ID NO: 4 (AEICLLPLDYGPCR).

According to some embodiments, said at least one peptide is consisting of the amino acid sequences set forth in SEQ ID NO: 5 (NNAEICLLPLDYGP).

According to some embodiments, said at least one peptide is consisting of the amino acid sequences set forth in SEQ ID NO: 6 (RYYYDRYTQSCRQF)

According to some embodiments, said at least one peptide is consisting of the amino acid sequences set forth in SEQ ID NO: 7 (NANNFYTWEAC).

According to some embodiments, said disease or disorder is selected from the group consisting of: cancer, cancer-associated thrombosis, a solid tumor associated with a malignant disease, myocardial infarction, unstable angina, atrial fibrillation, stroke, renal damage, percutaneous transluminal coronary angioplasty, disseminated intravascular coagulation, sepsis, gestational vascular complications, pulmonary embolism and deep vein thrombosis. Each possibility represents a separate embodiment of the present invention.

According to some embodiments, said disease or disorder is sepsis.

According to some embodiments, said disease or disorder is cancer-associated thrombosis.

According to some embodiments, said disease or disorder is abnormal clotting induced by a solid tumor.

According to some embodiments, said disease or disorder is abnormal clotting induced by a clinical procedure.

According to some embodiments, said clinical procedure is invasive.

According to some embodiments, treating a disease or disorder comprises applying a surgical procedure.

According to some embodiments, said at least one peptide is administered to said subject prior to said applying the surgical procedure.

According to some embodiments, said at least one peptide is administered to said subject during the surgical procedure.

According to some embodiments, there is provided a therapeutic composition comprising at least one peptide derived from the first or third Kunitz domain of tissue factor pathway inhibitor, for use in the treatment of a disease or disorder associated with abnormal clotting.

According to some embodiments, there is provided a kit for the treatment of a disease or disorder associated with abnormal clotting comprising a therapeutic composition comprising at least one peptide derived from the first or third Kunitz domain of tissue factor pathway inhibitor.

According to some embodiments, said kit comprises at least one peptide in the form of a pharmaceutical composition.

According to some embodiments, said kit further comprises at least one pharmaceutical carrier for reconstituting said at least one peptide.

According to some embodiments, there is provided a method for treating a solid tumor in a subject in need thereof comprising administering to the subject a therapeutic composition comprising at least one peptide derived from the first or third Kunitz domain of tissue factor pathway inhibitor.

According to some embodiments, in the method of treating a solid tumor said at least one peptide comprises the amino acid sequences set forth in SEQ ID NO: 8. According to some embodiments, in the method of treating a solid tumor said at least one peptide comprises an amino acid sequences selected from SEQ ID NOs: 3-5. Each possibility represents a separate embodiment of the present invention.

According to some embodiments, said treating is attenuating tumor size.

According to some embodiments, said treating comprises reducing the size of said solid tumor, inhibiting the development of said solid tumor, attenuating the rate of development of said solid tumor, preventing the development of said tumor, increasing survival rate of said subject, inhibiting tumor relapse, attenuating the rate of tumor relapse, and a combination thereof. Each possibility represents a separate embodiment of the present invention.

According to some embodiments, said solid tumor is breast cancer. According to some embodiments, said breast cancer is metastatic breast cancer. According to some embodiments, said solid tumor is melanoma. According to some embodiments, said melanoma is metastatic melanoma.

According to some embodiments, there is provided a therapeutic composition comprising at least one peptide derived from the first or third Kunitz domain of tissue factor pathway inhibitor for use in the treatment of a solid tumor.

According to some embodiments, there is provided use of a therapeutic composition comprising at least one peptide derived from the first or third Kunitz domain of tissue factor pathway inhibitor for the preparation of a medicament for the treatment of a solid tumor.

According to some embodiments, there is provided use of a therapeutic composition comprising at least one peptide derived from the first or third Kunitz domain of tissue factor pathway inhibitor for the treatment of a solid tumor.

According to some embodiments, said treatment comprises reduction of tumor size, inhibition of tumor growth, reduction in the rate of development of said solid tumor, prevention of the development of said tumor, inhibition of tumor relapse, reduction in the rate of tumor relapse, and a combination thereof. Each possibility represents a separate embodiment of the present invention.

According to some embodiments, there is provided a kit comprising at least one peptide derived from the first or third Kunitz domain of tissue factor pathway inhibitor for use in the treatment of a solid tumor.

According to some embodiments, the kit comprises at least one peptide comprising the amino acid sequences set forth in SEQ ID NO: 8. According to some embodiments, the kit comprises at least one peptide selected from SEQ ID NOs: 3-5. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 7A and 7B show the size of B16 mouse melanoma tumor in untreated C57BL/6 mice (con) and in mice treated with the peptides of SEQ ID NOs: 4 (A) and 5 (B) for 3 weeks, ***P<0.0001.

DETAILED DESCRIPTION OF THE INVENTION

The present invention provides peptides derived from TFPI, specifically, from the first or third Kunitz domain of TFPI for treating diseases or disorders associated with abnormal clotting and for treating solid tumors.

Tissue factor pathway inhibitor (TFPI) is a potent direct inhibitor of factor Xa, and in a factor Xa dependent fashion produces inhibition of the factor TF-VIIa complex which is involved in the coagulation cascade. In brief, blood coagulation cascade usually initiates as soon as the cell surface glycoprotein tissue factor (TF) comes into contact with circulating activated factor VII (Vila), resulting in the formation of TF-VIIa complex. The TF-VIIa complex activates X to factor Xa. Subsequently, factor Xa catalyzes the conversion of prothrombin to thrombin, thereby leading to fibrin formation, platelet activation, and, ultimately, generation of a thrombus.

According to the National Center for Biotechnology Information (NCBI) Blast database, peptides corresponding to SEQ ID NOs: 3-5 have 40% (6/15) identities to TFPI α and β amino-acids (AA) sequence 13-27 that is located in TFPI signal peptides (AA 1-28). In addition, peptides corresponding to SEQ ID NOs: 3 and 4 have 64% (7/11) identities to TFPI-α AA sequence 217-227 that is located at the third Kunitz domain (AA 217-268). No similar AA sequences to peptides corresponding to SEQ ID NOs: 2 and 7 were found in TFPI α or β molecules. Thus, without being bound by any theory or mechanism, as the signal peptide is usually degraded in the cell, the TFPI third Kunitz domain may potentially exert an inhibitory effect on heparanase procoagulant activity.

Figure 4A:
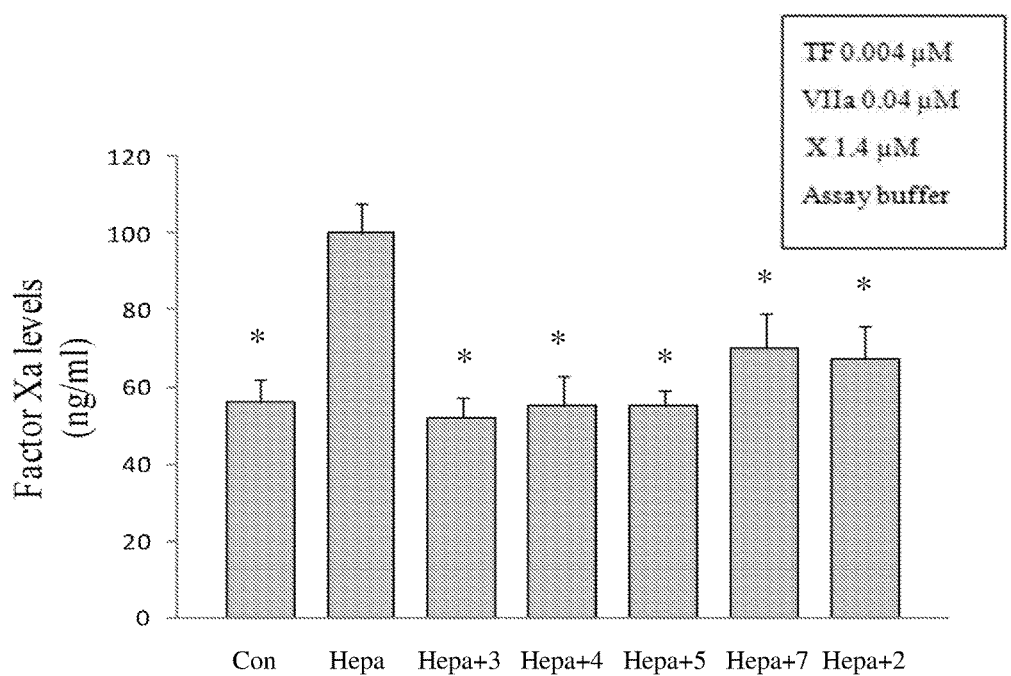
FIGS. 4A and 4B show factor Xa levels in HEK-293 control cells (con), cells treated with heparanase alone (Hepa) or heparanase with peptides of SEQ ID NOs: 2-5 and 7, *P<0.05 (A) and the corresponding co-immunoprecipitation (CO-IP) blots of the cell lysates with anti-Hepa (B, upper panel) and anti-TF (B, lower panel).
Figure 4B:
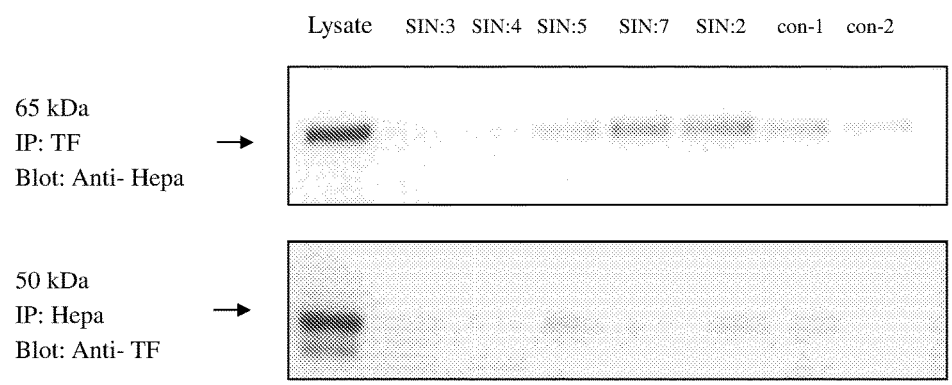
Figure 4C:
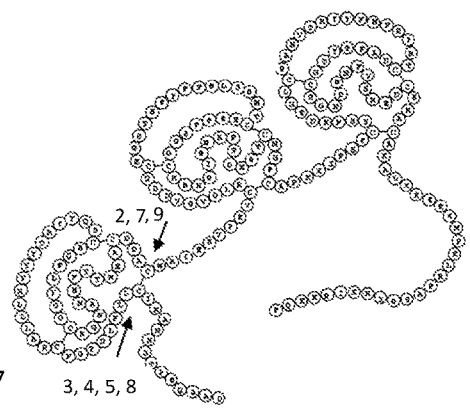
FIG. 4C is a cartoon representing the solvent accessible surface of TFPI-2 molecule first Kunitz domain, with arrows indicating the amino acid shared by the peptides of SEQ ID NOs: 2-5 and 7.
Figure 4D:
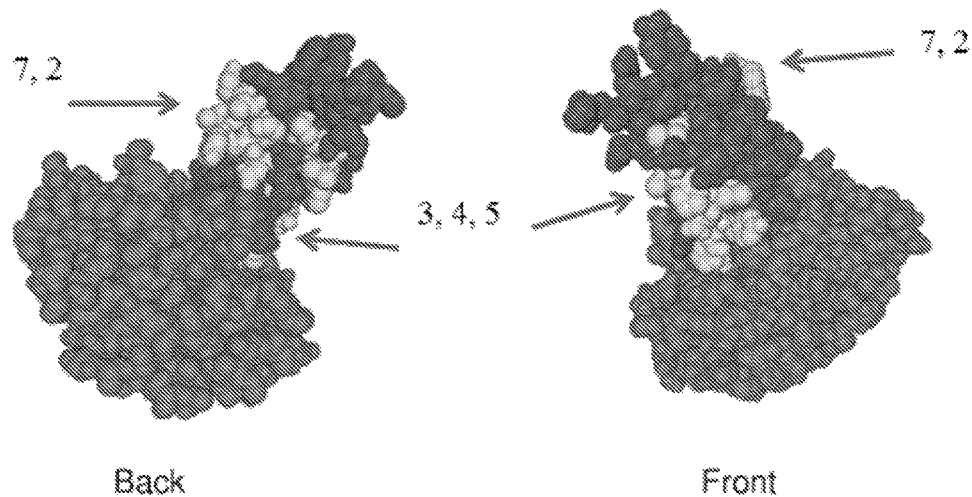
FIG. 4D is the predicted 3D structure of TFPI-2, showing the first Kunitz domain (dark) and the amino acid shared by peptides of SEQ ID NOs: 2-5 and 7 (light gray).

According to some embodiments, the inhibitory peptides of the invention are derived from the base of the first Kunitz domain in TFPI-2 (FIG. 4C).

While efficient clotting limits the loss of blood at an injury site, inappropriate formation of thrombi in veins or arteries is a common cause of disability and death. Abnormal clotting activity can result in, or from, pathologies or treatments of diseases, such as, cancer, myocardial infarction, unstable angina, atrial fibrillation, stroke, renal damage, percutaneous transluminal coronary angioplasty, disseminated intravascular coagulation, sepsis, gestational vascular complications, pulmonary embolism and deep vein thrombosis. The formation of clots on foreign surfaces of artificial organs, shunts and prostheses such as artificial heart valves is also problematic.

Thus, according to some embodiments, there is provided a method for treating a disease or disorder associated with abnormal clotting in a subject in need thereof comprising administering to the subject a therapeutic composition comprising at least one peptide derived from the first or third Kunitz domain of TFPI.

According some embodiments, said tissue factor pathway inhibitor is tissue factor pathway inhibitor-2.

According to some embodiments, said at least one peptide is consisting of 7-20 amino acids.

According to some embodiments, said at least one peptide comprises an amino acid sequences selected from SEQ ID NOs: 8 through 9 and combinations thereof. Each possibility represents a separate embodiment of the present invention.

According to some embodiments, said at least one peptide comprises an amino acid sequences selected from SEQ ID NOs: 1 through 9 and combinations thereof. Each possibility represents a separate embodiment of the present invention.

According to some embodiments, said at least one peptide comprises the amino acid sequence set forth in SEQ ID NO: 8 (ICLLPLDYGP). According to some embodiments, said at least one peptide comprises an amino acid sequences selected from SEQ ID NOs: 3 through 5 and combinations thereof. Each possibility represents a separate embodiment of the present invention.

According to some embodiments, said at least one peptide comprises the amino acid sequence set forth in SEQ ID NO: 9 (NNFYTWEAC). According to some embodiments, said at least one peptide comprises an amino acid sequences selected from SEQ ID NOs: 2 and 7 and combinations thereof. Each possibility represents a separate embodiment of the present invention.

Using the peptides of the invention for treating abnormal coagulation confers various advantages over known anticoagulants. For example, the peptides of the invention are water soluble, and are absorbed from subcutaneous injection. Furthermore, the peptides of the invention exert their effect for at least 4 hours. Moreover, assays for bleeding tendency by PTT, PT, anti Xa activity and TEG, indicated that in contrast to other anticoagulants that exert a bleeding tendency even when added to normal blood, the peptides of the invention do not cause bleeding, and only when there is activation of the coagulation system, and heparanase is released to the blood, probably from activated platelets, the peptides exert their inhibitory effect, by inhibiting the additional activation. However, the peptides of the invention do not interfere in the normal TF activity.

According to some embodiments, said disease or disorder is sepsis.

According to some embodiments, the disease or disorder is cancer.

According to some embodiments, the disease or disorder is cancer associated thrombosis.

According to some embodiments, said disease is cancer and said at least one peptide is administered in combination with chemotherapy.

According to some embodiments, said at least one peptide is administered topically. According to some embodiments, said at least one peptide is administered at the site of a tumor. According to some embodiments, said at least one peptide is administered at the site of a surgery, before the surgery is performed. According to some embodiments, said at least one peptide is administered at the site of a surgery, during the surgery. According to some embodiments, said at least one peptide is administered at the site of a surgery after the surgery has been performed.

The at least one peptide may be administered by oral, buccal, pulmonary, parenteral (intramuscular, intraperitoneal, intravenous, or subcutaneous injection), inhalational (via a fine powder formulation, or aerosol), transdermal, nasal, vaginal, rectal, or sublingual routes of administration and may be formulated in dosage forms appropriate for each route of administration. See, for example, WO 93/25221 and WO 94/17784. Each possibility represents a separate embodiment of the present invention.

Figure 5A:
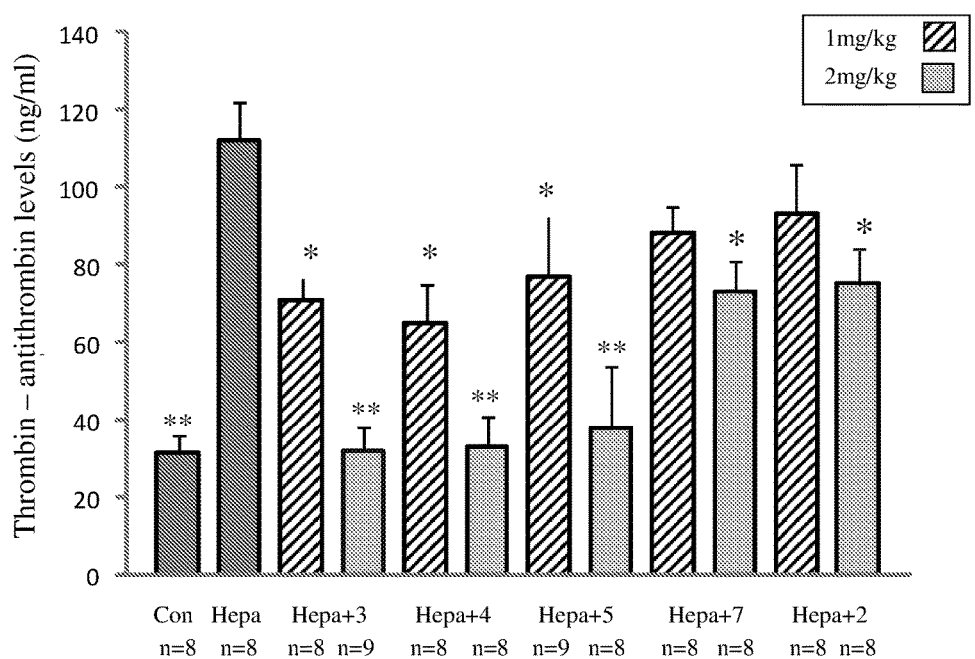
FIG. 5A shows thrombin-antithrombin (TAT) levels in the plasma of ICR mice, untreated (control), and 4 hours after administration of heparanase alone (Hepa) or heparanase with peptides of SEQ ID NOs: 2-5, 7 at a concentration of 1 mg/kg (dashed fill) or 2 mg/kg (solid fill), *P<0.05.
Figure 5B:
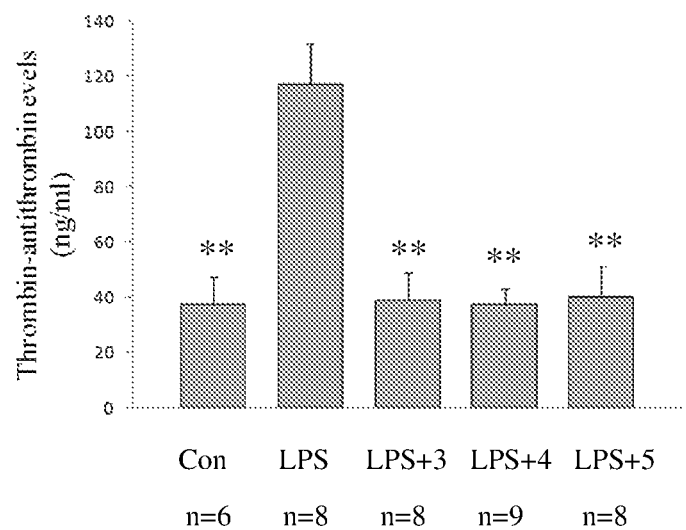
FIGS. 5B and 5C shows TAT (5B) and IL-6 (5C) levels in the plasma of ICR mice, untreated (control), and following administration of LPS alone or with peptides of SEQ ID NOs: 3-5, P<0.001, *P<0.0001.

As exemplified hereinbelow, a significant decrease in activation of the coagulation system was shown in the LPS induced sepsis model (FIG. 5B). Without being bound by any theory or mechanism, these results indicate that the role of the peptides is to attenuate the activation of the coagulation system during sepsis, thereby preventing a main cause of increased morbidity and mortality in patients. LPS, produced by gram negative bacteria, is known to induce exposure of TF on endothelial cells surface within minutes. Hence, the successful inhibition of coagulation activation by the peptides of the invention may be due to the fact that it is carried out by inhibiting TF activation—one of the main triggers to coagulation activation.

According to some embodiments, treating a disease or disorder comprises applying a surgical procedure.

According to some embodiments, said at least one peptide is administered to said subject prior to said applying the surgical procedure.

According to some embodiments, said at least one peptide is administered to said subject during the surgical procedure.

According to some embodiments, said abnormal clotting is induced by cancer. According to some embodiments, said abnormal clotting is induced by a clinical procedure. According to some embodiments, said clinical procedure is invasive. According to some embodiments, said clinical procedure is surgery.

According to some embodiments, the at least one peptide is provided in the form of a pharmaceutical composition. It should be noted that the at least one peptide is generally administered in the form of a pharmaceutical composition together with a pharmaceutically acceptable carrier or diluent, and optionally a further therapeutic agent.

The pharmaceutical composition containing the at least one peptide may be administered for prophylactic and/or therapeutic treatments. In therapeutic applications, the pharmaceutical composition is administered to a patient already suffering from a disease or disorder associated with abnormal clotting, as described above, in an amount sufficient to cure or at least partially arrest the symptoms of the disease or disorder and their complications. An amount adequate to accomplish such effect is defined as "therapeutically effective dose". Amounts effective for this use will depend on the severity of the disease and the weight and general state of the patient.

The pharmaceutical composition may be administered as a single dose or in multiple doses; administered either as individual therapeutic agents or in combination with other therapeutic agents; and combined with conventional therapies, which may be administered sequentially or simultaneously. Each possibility represents a separate embodiment of the present invention.

According to some embodiments, the at least one peptide is an artificial peptide. According to some embodiments, the at least one peptide is synthesized ex vivo.

According to some embodiments, the at least one peptide is tagged by a detectable marker.

According to some embodiments, the at least one peptide is linked to a therapeutic agent. According to some embodiments, the therapeutic agent is a chemotherapeutic drug. According to some embodiments, the therapeutic agent is a toxin.

According to some embodiments, the at least one peptide is a plurality of peptides. It should be noted that different combinations of different ratios at different concentrations of the peptides set forth in SEQ ID NOs: 1-9 may be used for different diseases or disorders.

According to some embodiments, there is provided a therapeutic combination comprising at least one peptide selected from SEQ ID NOs: 1-9 and at least one other active therapeutic agent. Each possibility represents a separate embodiment of the present invention.

According to some embodiments, there is provided a pharmaceutical composition comprising at least one peptide derived from the first or third Kunitz domain of tissue factor pathway inhibitor, for use in the treatment of a disease or disorder associated with abnormal clotting.

According to some embodiments, there is provided use of a pharmaceutical composition comprising at least one peptide derived from the first or third Kunitz domain of tissue factor pathway inhibitor, for the treatment of a disease or disorder associated with abnormal clotting.

According to some embodiments, there is provided use of a pharmaceutical composition comprising at least one peptide derived from the first or third Kunitz domain of tissue factor pathway inhibitor, for the preparation of a medicament for the treatment of a disease or disorder associated with abnormal clotting.

According to some embodiments, there is provided a pharmaceutical composition comprising one or more of the peptides derived from the first or third Kunitz domain of tissue factor pathway inhibitor as the active ingredients and at least one with a pharmaceutical carrier or diluent.

According to some embodiments, the pharmaceutical composition is in a form appropriate for the desired route of administration, including, but not limited to, the following routes: oral, pulmonary, parenteral, inhalational, transdermal, nasal, vaginal, rectal, or sublingual. Each possibility represents a separate embodiment of the present invention.

According to some embodiments, the pharmaceutical composition is in a solid dosage form. Solid dosage forms for oral administration include capsules, tablets, pills, powders, and granules. In such solid dosage forms, the active compound is admixed with at least one inert pharmaceutically acceptable carrier such as sucrose, lactose or starch. Such dosage forms can also comprise, as is normal practice, additional substances other than inert diluents, for example, lubricating agents such as magnesium stearate. In the case of capsules, tablets, and pills, the dosage forms may also comprise buffering agents. Tablets and pills can additionally be prepared with enteric coatings. Each possibility represents a separate embodiment of the present invention.

According to some embodiments, the pharmaceutical composition is in a liquid dosage form for oral administration. Such dosage forms include pharmaceutically acceptable emulsions, solutions, suspensions and/or syrups, with the elixirs containing inert diluents commonly used in the art, such as water. Besides such inert diluents, the compositions may also include adjuvants, such as wetting agents, emulsifying and suspending agents, and sweetening, flavoring, and perfuming agents. Each possibility represents a separate embodiment of the present invention.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use. Each possibility represents a separate embodiment of the present invention.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

According to some embodiments, the pharmaceutical composition may be a microencapsulated composition.

According to some embodiments, the pharmaceutical composition further comprises at least one other active therapeutic agent. The additional therapeutic agent may be capable of addressing at least one coagulation-related abnormality or may enhance the anticoagulation effect exerted by the at least one peptide.

According to some embodiments, the present invention provides a kit comprising a therapeutic composition comprising at least one peptide derived from the first or third Kunitz domain of tissue factor pathway inhibitor, for use in the treatment of a disease or disorder associated with abnormal clotting.

According to some embodiments, the kit comprises the peptide of SEQ ID NO: 1 and homologs thereof. According to some embodiments, the kit comprises the peptide of SEQ ID NO: 2 and homologs thereof. According to some embodiments, the kit comprises the peptide of SEQ ID NO: 3 and homologs thereof. According to some embodiments, the kit comprises the peptide of SEQ ID NO: 4 and homologs thereof. According to some embodiments, the kit comprises the peptide of SEQ ID NO: 5 and homologs thereof. According to some embodiments, the kit comprises the peptide of SEQ ID NO: 6 and homologs thereof. According to some embodiments, the kit comprises the peptide of SEQ ID NO: 7 and homologs thereof. According to some embodiments, the kit comprises the peptide of SEQ ID NO: 8 and homologs thereof. According to some embodiments, the kit comprises the peptide of SEQ ID NO: 9 and homologs thereof.

According to some embodiments, the kit further comprises means for administering said peptides.

According to some embodiments, the at least one peptide is provided in a lyophilized form. According to some embodiments, the kit further comprises a pharmaceutical carrier for reconstituting said peptide.

According to some embodiments, the kit comprises one or more packs, each comprising the at least one peptide in a form ready for administration. In some embodiments, the kit comprises one or more packs, each comprising the at least one peptide in a form ready for use. In some embodiments, the kit comprises said one or more packs, and optionally the pharmaceutical carrier required to prepare the at least one peptide for use. According to some embodiments, the kit comprises the pharmaceutical carrier in a separate pack.

According to some embodiments, the kit may include other components, e.g., instructions for dilution, mixing and/or administration of the at least one peptide, other containers, syringes, needles, etc. Other such pack/kit components will be readily apparent to one of skill in the art. Each possibility represents a separate embodiment of the present invention.

According to some embodiments, the present invention provides a method for treating cancer in a subject in need thereof comprising administering to the subject a therapeutic composition comprising at least one peptide derived from the first or third Kunitz domain of tissue factor pathway inhibitor.

According to some embodiments, said cancer comprises a solid tumor.

According to some embodiments, said solid tumor is selected from the group consisting of: oral: buccal cavity, lip, tongue, mouth, pharynx; cardiac: sarcoma (angiosarcoma, fibrosarcoma, rhabdomyosarcoma, liposarcoma), myxoma, rhabdomyoma, fibroma, lipoma and teratoma; lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor (nephroblastoma), lymphoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver: hepatoma (hepatocellular carcinoma), cholangiocarcinoma, hepatoblastoma, angiosarcoma, hepatocellular adenoma, hemangioma, biliary passages; bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and adrenal glands: neuroblastoma. Each possibility represents a separate embodiment of the present invention.

According to some embodiments, in the method of treating a solid tumor said at least one peptide comprises the amino acid sequences set forth in SEQ ID NO: 8. According to some embodiments, in the method of treating a solid tumor said at least one peptide comprises an amino acid sequences selected from SEQ ID NOs: 3-5. Each possibility represents a separate embodiment of the present invention.

According to some embodiments, said treating is attenuating tumor size.

Surprisingly, as exemplified herein, the peptides of the invention were shown to reduce tumor size in various types of tumors, slow down the rate of tumor development and slow down the rate of tumor progression. Moreover, the peptides were shown to prevent, delay or attenuate tumor relapse. In addition, the peptides of the invention increased the rate of survival in animals bearing tumors.

According to some embodiments, said treating comprises reducing the size of said solid tumor, inhibiting the development of said solid tumor, attenuating the rate of development of said solid tumor, preventing the development of said tumor, increasing survival rate of said subject, inhibiting tumor relapse, attenuating the rate of tumor relapse, and a combination thereof.

According to some embodiments, said solid tumor is breast cancer. According to some embodiments, said breast cancer is metastatic breast cancer.

According to some embodiments, said solid tumor is melanoma. According to some embodiments, said melanoma is metastatic melanoma.

According to some embodiments, there is provided a kit comprising a therapeutic composition comprising at least one peptide derived from the first or third Kunitz domain of tissue factor pathway inhibitor, for use in the treatment of a solid tumor.

The terms "comprises", "comprising", "includes", "including", "having" and their conjugates mean "including but not limited to". This term encompasses the terms "consisting of" and "consisting essentially of". As used herein, the singular form "a", "an", "the" and "said" include plural references unless the context clearly dictates otherwise. For example, the term "a compound" or "at least one compound" may include a plurality of compounds, including mixtures thereof.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1. TF/Heparanase Inhibitory Peptides In-Vitro

Materials and Methods:

Transgenic mouse model in which human heparanase expression is driven by the β-actin promoter, thus enabling high levels of expression in essentially all tissues, was utilized in BALB/C background mice. Heparanase knock-out (KO) mice were generated in C57BL/6 mice using a KO construct designed to delete a 3.2 kb region that includes a part of the hpa-promoter, the first exon and part of the first intron Amplification of three pairs of primers that cover the full-length mouse heparanase coding sequence yielded no product in the mutant animals, confirming knock-out of the gene.

HEK-293 cells grown in Dulbecco's modified Eagle's medium supplemented with 10% fetal calf serum and antibiotics were stably transfected with full-length human heparanase (65 kDa) cDNA cloned into the pSecTag2 vector (Invitrogen, Carlsbad, Calif., USA). Transfection proceeded for 48 h, followed by selection with Zeocin (Invitrogen, Carlsbad, Calif., USA) for 2 weeks. Stable transfectant pools were further expanded and analyzed.

Single chain GS3 heparanase gene construct, comprising the 8 and 50 kDa heparanase subunits (8+50) was purified from the conditioned medium of baculovirus-infected cells. GS3 heparanase was assayed for the presence of bacterial endotoxin by Biological Industries (Beit Haemek, Israel), using the gel-clot technique (Limulus amebocyte lysate—LAL test) and was found to contain <10 pg/ml endotoxin. Polyclonal antibody 1453 was raised in rabbits against the entire 65 kDa heparanase precursor isolated from the conditioned medium of heparanase-transfected HEK-293 cells. The antibody was affinity-purified on immobilized bacterially expressed 50 kDa heparanase GST fusion protein. Monoclonal antiheparanase antibody 1E1 was generated by immunizing BALB/C mice with the entire 65 kDa heparanase protein. Lipidated recombinant human TF and monoclonal and polyclonal antihuman TF antibodies were purchased from American Diagnostica (Stanford, Conn., USA). Recombinant human factor VIIa and plasma-derived human factor X were purchased from American Diagnostica (Stanford, Conn.). All coagulation factors were dissolved in double-distilled water. Chromogenic substrate to factor Xa (I.D. 222, solubility: Tris buffer, pH −8.4) was purchased from American Diagnostica (Stanford, Conn.). Lipopolysaccharides (LPS) was obtained from Sigma (St. Louis, Mo.).

Plasma preparation was carried out as follows: the prothrombin time (PT), activated partial thromboplastin time (PTT) and fibrinogen were measured in fresh platelet-poor plasma, prepared by centrifugation at 2000 g for 15 min. For other plasma assays, following a second centrifugation at 2000 g for 15 min, plasma aliquots were frozen at −70±5° C. Plasma aliquots for assays were thawed only once by placing them in a water bath at 37±0.5° C. for 15 min.

PT, PTT, fibrinogen and anti-Xa level assays were performed on the STA-R analyzer using recombinant human thromboplastin Dade® Innovin® (Dade Behring Marburg GmbH, Germany) for the PT. STA-PTT®, STA-FIBRINOGEN and STA®-Liquid Anti-Xa were used for the PTT, fibrinogen and anti-Xa level (Diagnostica STAGO, France).

Thrombin-antithrombin complex (TAT) complex was evaluated according to the manufacturer recommendations by Enzygnost® TAT micro ELISA purchased from Siemens (Marburg, Germany). D-dimer assay was performed on the STA-R evolution analyzer (Diagnostica Stago) using recombinant STA-LIATEST D-DI kit (Diagnostica Stago).

Thromboelastography assay was performed according to the manufacturer recommendations. Briefly, blood was collected in a bottle containing 3.2% (0.12M) sodium citrate (9:1) and stored at room temperature. Recalcification and TEG® measurements at 37° C. were performed in disposable cups of the Thrombelastograph® coagulation analyzer (Haemoscope Corporation, Skokie, Ill.).

Proteins were subjected to 10% SDS-polyacrylamide gel electrophoresis (PAGE) and transferred to polyvinylidene fluoride membrane (BioRad, Maylands, Calif.). The membrane was probed with the appropriate antibody followed by horseradish peroxidase (HRP)-conjugated secondary antibody (Jackson ImmunoResearch, West Grove, Pa.) and chemiluminescence substrate (Pierce, Rockford, Ill.), as described.

The interaction between TF and heparanase was analyzed by co-immunoprecipitation (CO-IP). The ProFound™ Co-Immunoprecipitation Kit in which the antibody is coupled to gel support, was employed according to the manufacturer's (Pierce, Rockford, Ill.) instruction. Briefly, coupling gel was washed with coupling buffer. Polyclonal anti-TF or polyclonal anti-heparanase (1453) antibodies (100 μg) and 5 M sodium cyanoborohydride were added to the gel support and incubated at 4° C. for 4 h. The gel was then washed with quenching buffer and incubated with the quenching buffer and sodium cyanoborohydride at 20° C. for 30 minutes. Next, the gel was washed four times with wash solution, once with elution buffer, and twice with coupling buffer. Lysate (100 μg) of HEK-293 cells transfected to overexpress heparanase 65 kDa was added to the gel and incubated for 2 hours at room temperature. The gel was washed four times with coupling buffer and bound proteins were eluted with elution buffer (pH 2.5), neutralized by 1 M Tris-HCl, pH 9.5, and subjected to immunoblot analysis. Monoclonal anti-TF and monoclonal anti-heparanase antibodies were used to detect the respective coupled protein. Irrelevant anti-GST polyclonal antibody (100 μg) and uncoupled beads were used as controls.

Data was evaluated by SPSS software for Windows version 13.0 (SPSS Inc., Chicago, Ill.). Statistics was calculated by non-parametric Mann-Whitney U test and T-TEST for independent variables. Value was reported as mean±SD. Significance level was set at $p<0.05$.

Figure 1A:
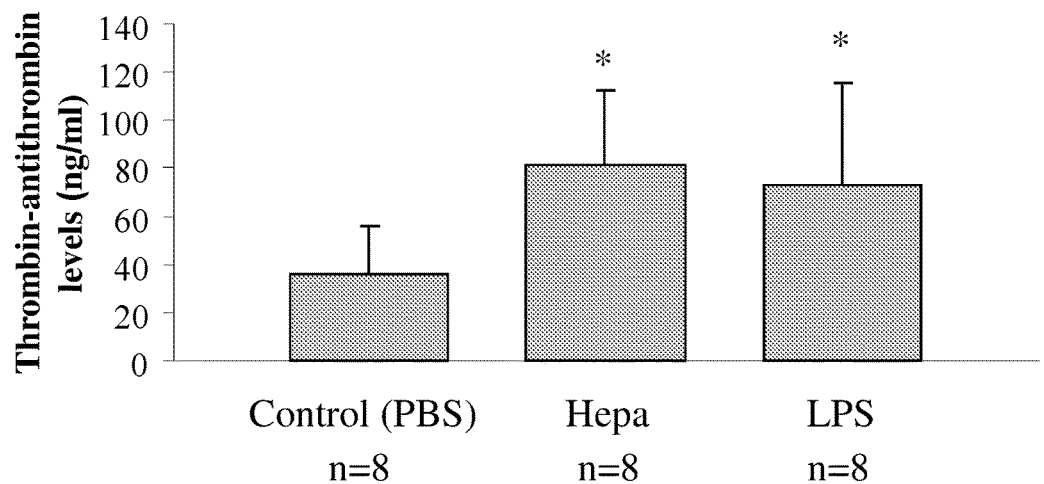
FIG. 1 shows heparanase coagulation activity in an ICR mice model treated with PBS (control), heparanase (Hepa) and LPS, through measurements of thrombin-antithrombin levels (A), D-dimer levels (B) and IL-6 levels (C), *P<0.05.
Figure 1B:
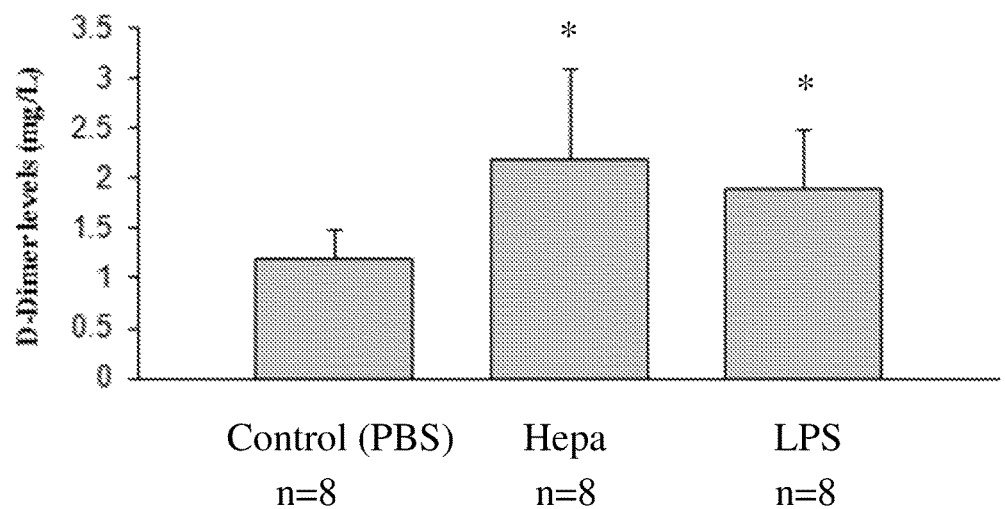
Figure 1C:
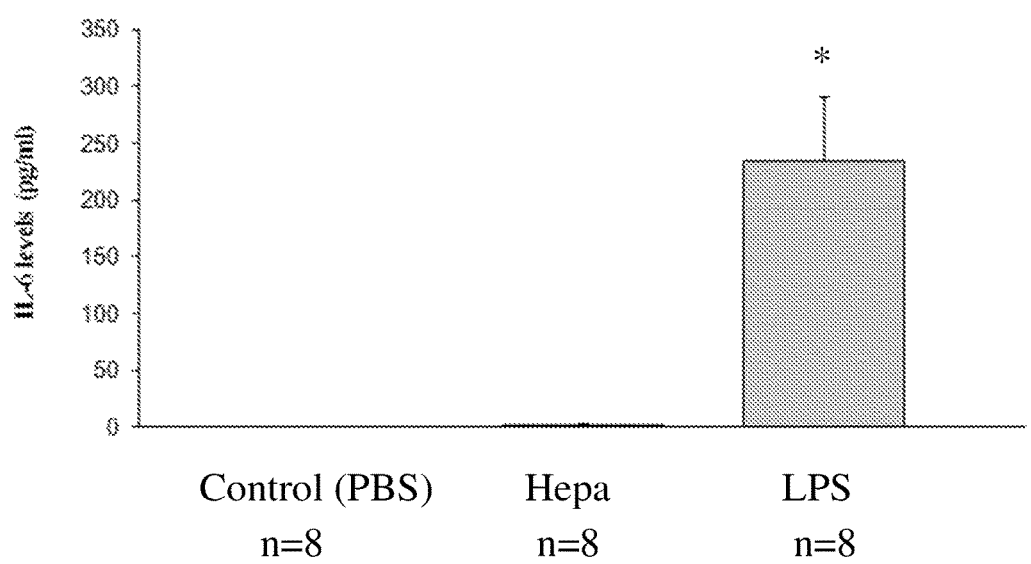

Results:

Material and method used as in Example 1. Heparanase (Hepa) was injected intra-peritoneal at a dose of 0.5 mg/kg to ICR mice. After 4 hours blood was drawn and the plasma was studied by ELISA to thrombin-antithrombin complex (TAT), D-Dimer as markers of coagulation activation and IL-6 as marker of sepsis severity. Please note that when compared with the control group (PBS) heparanase (Hepa) increased the levels of TAT and D-Dimer in a similar magnitude to that of LPS injected at a dose of 5 mg/kg that cause a moderate sepsis (FIG. 1A, B). Heparanase, however, did not increase IL-6 level compared with the control group and mice did not look ill (FIG. 1C), *$P<0.05$.

Example 2. Heparanase Contribution to Coagulation Activation in Sepsis

Figure 2A:
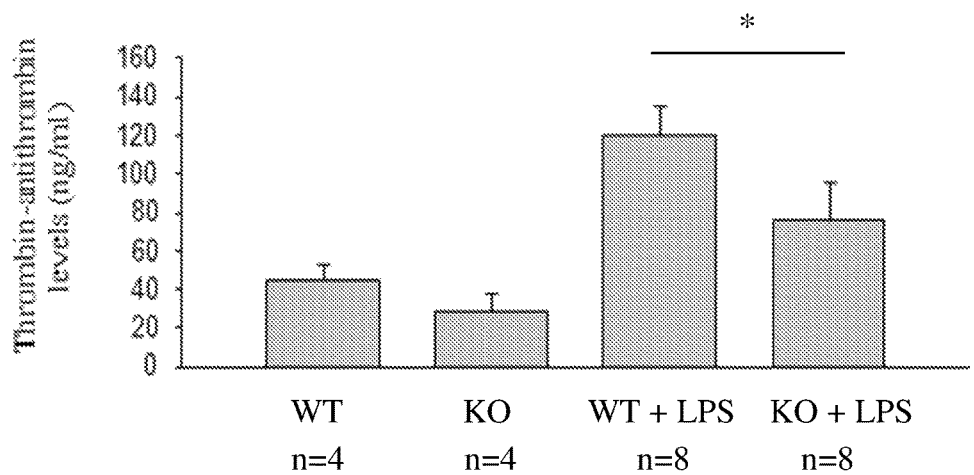
FIG. 2 shows levels of IL-6 and thrombin-antithrombin (TAT) after injection of LPS to heparanase knock-out (KO) mice compared to the wild type (WT) C57BL/6 mice, *P<0.05.
Figure 2B:
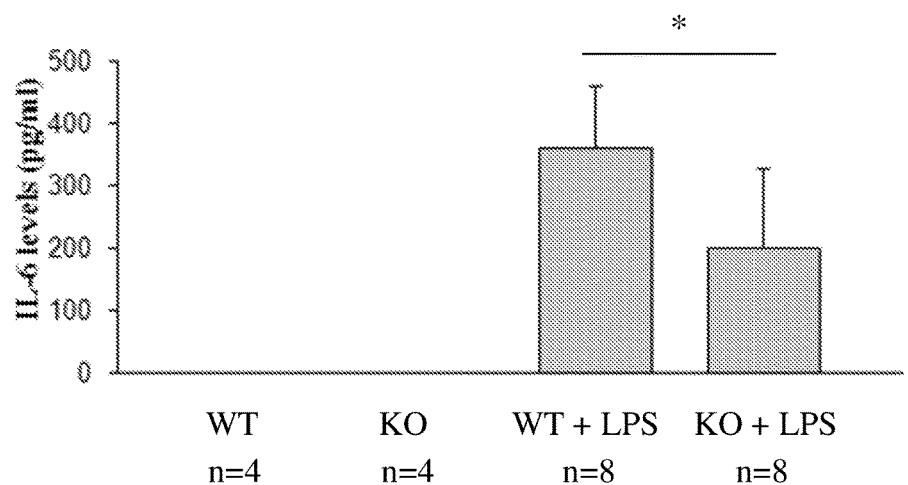

In heparanase knock-out (KO) mice, injection of LPS (5 mg/kg) resulted with a decrease in the levels of TAT (FIG. 2A) and IL-6 (FIG. 2B) compared to the wild type (WT) C57BL/6 mice. These results indicate that in the absence of heparanase the sepsis severity is attenuated and the activation of the coagulation system is reduced, *P<0.05.

Example 3. Heparanase Over-Expression in Mice and Sepsis

Figure 3A:
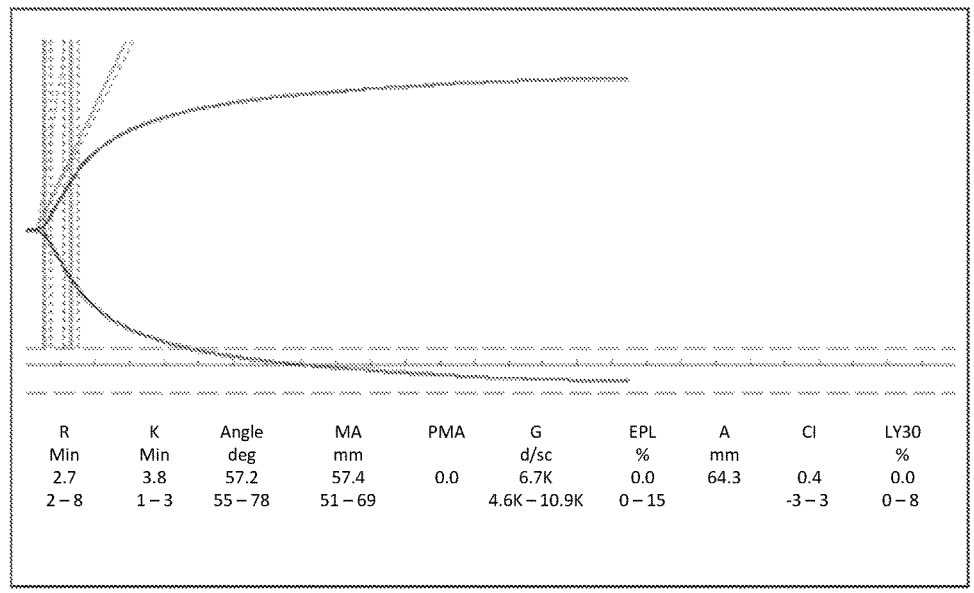
FIG. 3 shows thromboelastograph (TEG) from wild type BALB/C (WT) mice (A), WT mice 4 hours after being injected i.p. with LPS (B), mice with heparanase over-expression (C) and mice with heparanase over-expression 4 hours after injection of LPS (D).

Representative thromboelastographs (TEGs) of wild type (WT) BALB/C mice before and after administration of LPS are shown in FIGS. 3A-3D. The overall study included groups of 4 mice for each treatment. Activation was carried out by addition of calcium (FIG. 3A). LPS was injected to WT mice intra-peritoneal (5 mg/kg). Blood was drawn after 4 hours and immediately subjected to TEG. The following parameters were measured: reaction time until first clot (R), time from the end of R until the clot reaches 20 mm (K), the tangent of the curve made as the K is reached (Angle), maximum amplitude (MA), predefined maximum amplitude (PMA), log-derivation of the MA (G), estimated percent lysis (EPL), alpha (A), coagulation index (CI) and clot lysis percentage at 30 minutes (LY30).

Figure 3B:
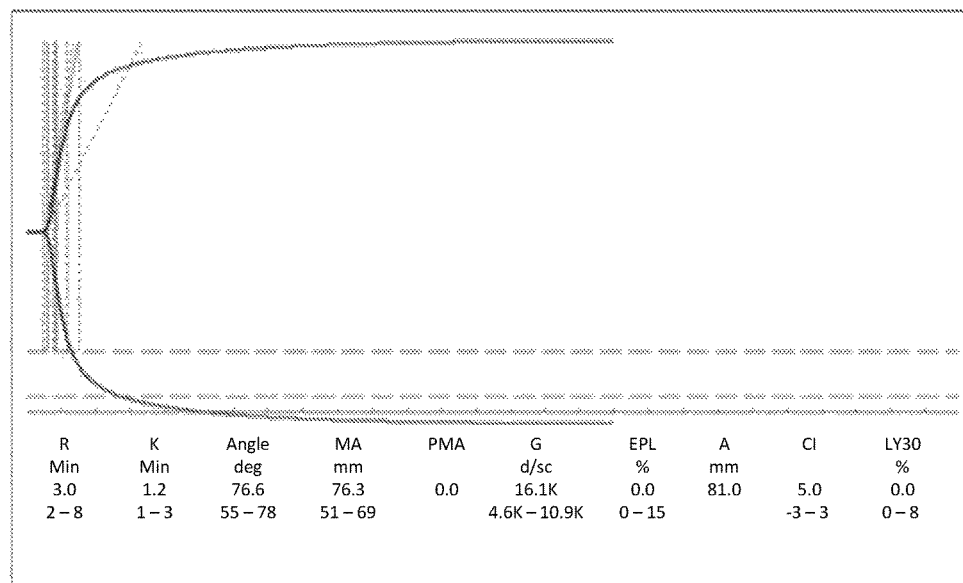
Figure 3C:
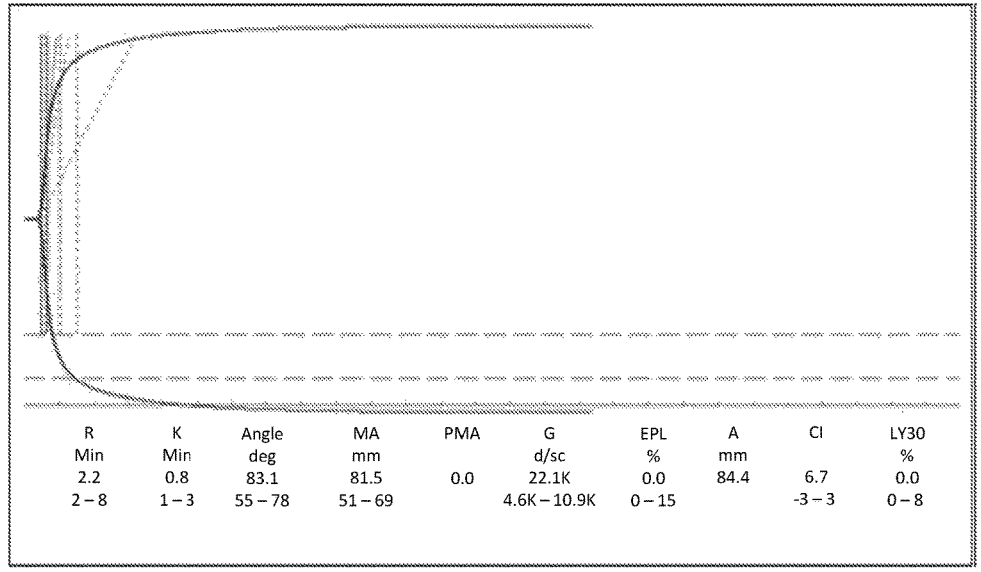
Figure 3D:
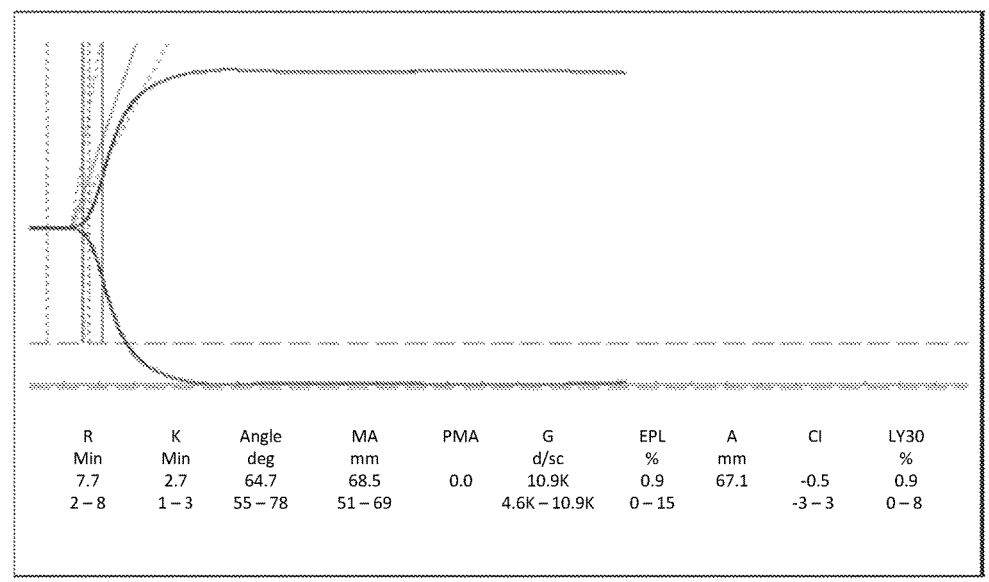

Maximal amplitude (MA) was significantly increased indicating an increase in clot strength (FIG. 3B). TEG of heparanase over-expression mice. MA was significantly increased (FIG. 3B) compared to WT mice (FIG. 3A) indicating again an increase in clot strength. LPS was injected to heparanase-over expression mice (FIG. 3D) as described in above with respect to FIG. 3B. As shown in FIG. 3D, LPS injection resulted with prolonged time to clot formation (R=7.7 min) and reduced MA (MA=68.5 mm), indicating severe consumption coagulopathy.

As TFPI and more specifically, TFPI-2, inhibited the procoagulant activity of heparanase on TF, 24 potential peptides were generated from the TFPI-2 molecule. The peptides effect was studied in an in-vitro assay that included lapidated TF, factor VIIa, factor X and buffer (0.06 M Tris, 0.04 M NaCl, 2 mM CaCl$_2$, 0.04% bovine serum albumin, pH 8.4). After 15 minutes of incubation, chromogenic substrate to Xa detection was added. It is noted that in this assay, the level of Xa increases upon addition of heparanase. Each of the peptides (dissolved in PBS) were added prior to heparanase. Upon addition of any one of the peptide comprising the consensus amino acid sequence corresponding to SEQ ID NO: 8 or SEQ ID NO: 9, such as, SEQ ID NOs: 2-5 and SEQ ID NO: 7, a significant decrease or abolishment of the heparanase procoagulant activity was observed, as expressed by diminished level of Xa (FIG. 4A). The peptides corresponding to SEQ ID NOs: 2-5 and SEQ ID NO: 7 did not inhibit the contribution of TF to Xa generation as further shown in FIG. 4A. Thus, the coagulation system remains activated in the presence of peptides comprising SEQ ID NO: 8 or SEQ ID NO: 9, and only the heparanase-induced excess activation is abolished in the presence of these peptides.

In-order to further establish this observation, peptides comprising SEQ ID NO: 8 or SEQ ID NO: 9 were added to whole blood at a dose of 25 µg/ml and immediately subjected to the tests of PT (Prothrombin time), PTT (Partial thromboplastin time), fibrinogen level, anti-Xa level and TEG. Representative results with the peptide set forth in SEQ ID NO: 4 are shown in Table 1 in mean values obtained from triplicates. As shown in the Table, no effect due to the peptides was observed compared to control plasma (Table 1, NS—not significant), supporting the assertion that, in contrast to other anticoagulant drugs, the peptides do not interfere in the normal hemostasis.

TABLE 1

| Assay | Control | With peptide (25 µg/ml) | P value |
|---|---|---|---|
| PT (seconds) | 10 | 10 | NS |
| PTT (seconds) | 31 | 30 | NS |
| Anti-Xa level (U/ml) | 0 | 0 | NS |
| Thrombin time (seconds) | 14 | 14 | NS |
| Fibrinogen (mg/dL) | 298 | 296 | NS |

Previously a direct protein-protein interaction between TF and heparanase by co-immunoprecipitation (CO-IP) was shown. In order to strengthen the specific inhibitory effect of the peptides, Lysate of HEK-293 cells transfected to over-express heparanase was incubated for 2 hours with beads coupled to polyclonal anti-TF (upper panel), or anti-heparanase (lower panel) antibodies. Bound proteins were analyzed by immunoblotting for the presence of heparanase (upper, left) or TF (lower, left), using the respective antibody demonstrating a significant inhibitory effect on TF and heparanase complex by the peptides of SEQ ID NOs: 2-5 and 7 (FIG. 4B). Note that when the peptides were added to the lysate prior to incubation (25 µg/ml) a significant decrease in the direct interaction between TF and heparanase was observed. Controls were beads coupled to irrelevant anti-GST polyclonal antibody (con-1) or uncoupled beads (con-2). A structural common mechanism was searched to the five peptides. When compared to the published structure of TFPI-2 by Sprecher et al. (Proc. Natl. Acad. Sci. USA 1994, 91:3353-3357) the base of the first Kunitz domain was found to be involved in the inhibition of TF/heparanase complex (FIG. 4C).

Figure 6A:
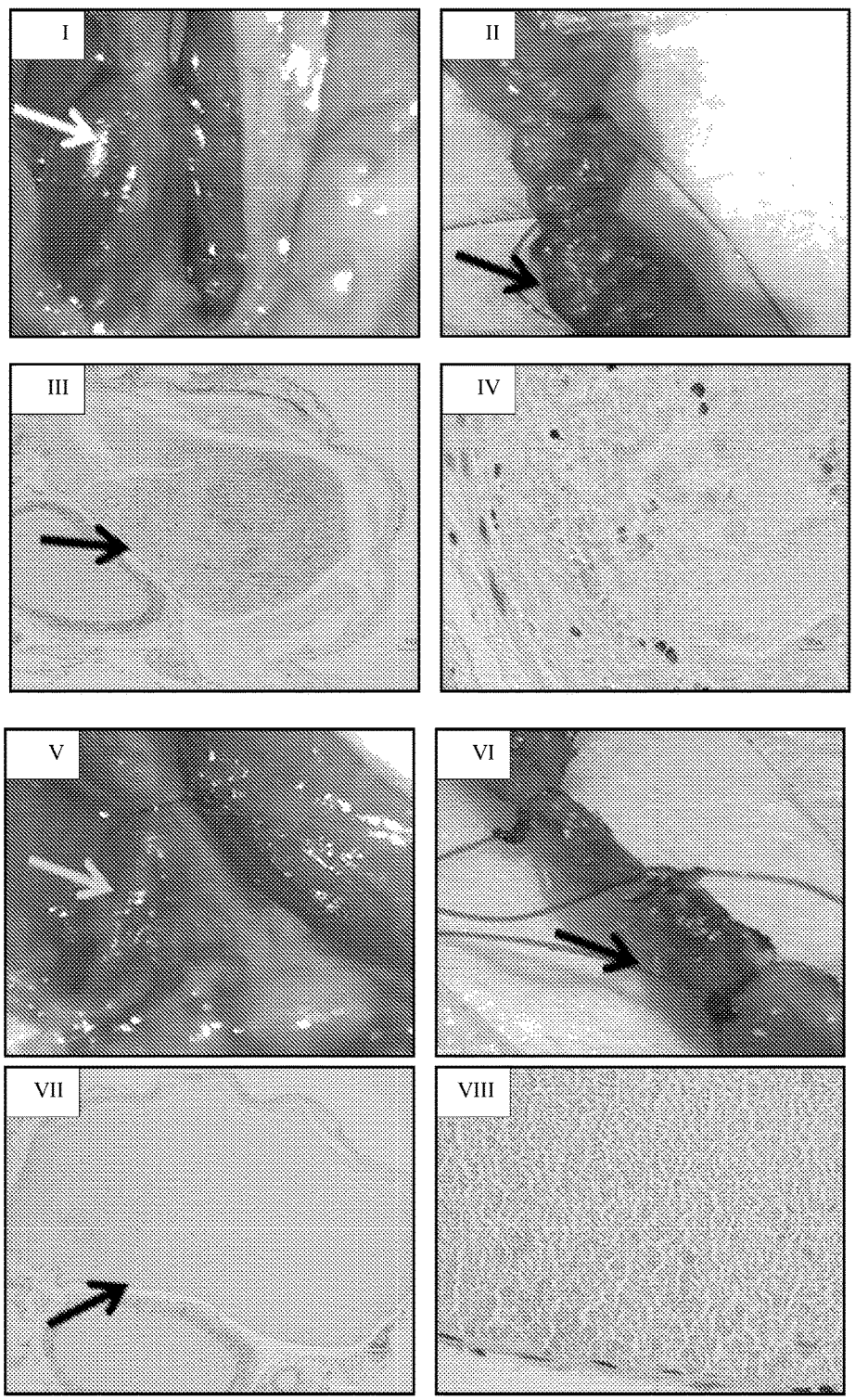
FIG. 6A are photographs (panels I, II, V, VI) of the inferior vena cava (IVC) in a thrombosis model and the corresponding histological sections stained with H&E (panels III, IV, VII, VIII), prior to treatment (panels I-IV) and following treatment with the peptides of SEQ ID NOs: 3-5 (panels V-VIII), with arrows pointing at a large thrombus located distal to the IVC ligation before (panels I and V) and after IVC was harvested (panels II and VI).
Figure 6B:
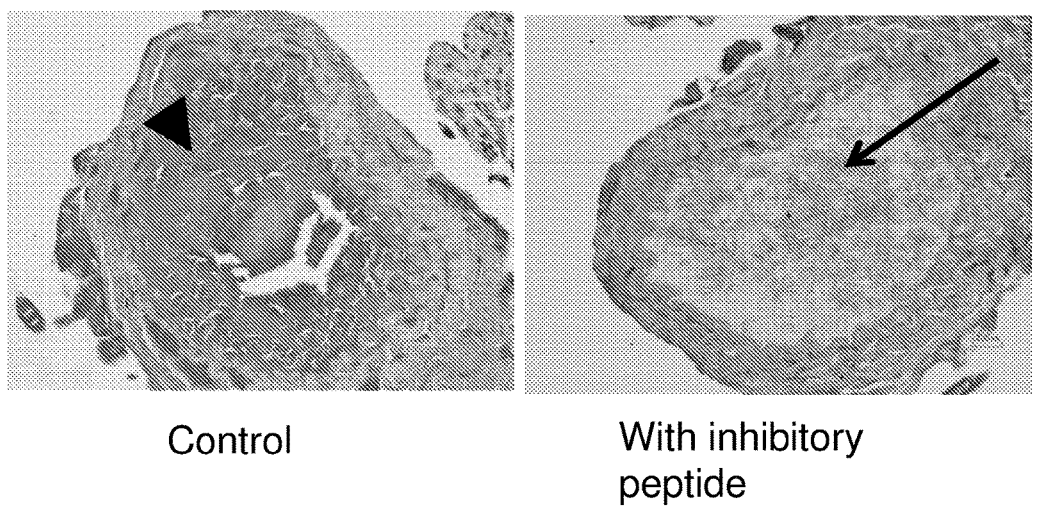
FIG. 6B shows histological sections of an arterial thrombus in the carotid artery of a control mouse (left panel) and a mouse treated with 2 mg/kg of the peptide of SEQ ID NO: 4 (right panel), 24 hours after completion of the experiment described in FIG. 6A and Example 4.

In a complimentary experiment, mice returned to normal activity after being subjected to stenosis of 90% of the carotid artery. 24 hours later mice were sacrificed. Sections of the carotid artery were analyzed by MSB (Martin, Scarlet, Blue) staining. In the treatment group, following a single s.c. injection of the peptides, almost no fibrin (thrombus) was formed, while in the control group large arterial thrombus was observed. The results are exemplified in FIG. 6B for a control mouse (left panel) and a mouse treated with 2 mg/kg of the peptide set forth in SEQ ID NO: 4 (right panel). As shown in the figure, early thrombus was observed in the treated mouse (FIG. 6B, right panel, arrow) while a large thrombus was observed in the control mouse (FIG. 6B, right panel, arrowhead).

Example 4. TF/Heparanase Inhibitory Peptides In-Vivo

Heparanase (Hepa) was injected intra-peritoneal to ICR mice at a dose of 0.5 mg/kg. After 30 min. peptides corresponding to SEQ ID NOs: 2-5 and 7 were injected at a dose of 1 mg/kg (dashed fill) or 2 mg/kg (solid fill) subcutaneously between the shoulders, into the loose skin over the neck. Blood was drawn after 4 hours, and the plasma was analyzed by ELISA for thrombin-antithrombin (TAT) levels. Peptides comprising SEQ ID NO: 8, corresponding to SEQ ID NOs: 3-5, abolished the procoagulant effect of heparanase in a dose dependent manner, while peptides comprising SEQ ID NO: 9, corresponding to SEQ ID NOs: 2 and 7 partially inhibited the procoagulant effect, as detected by levels of TAT (FIG. 5A).

Figure 5C:
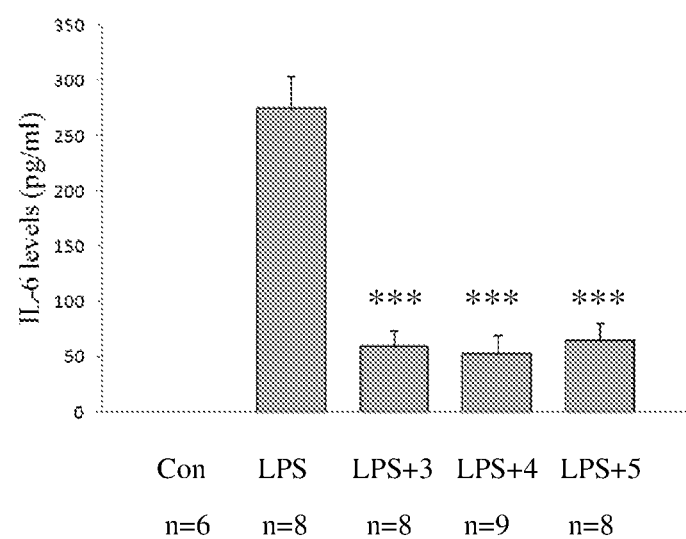

The therapeutic effect of the peptides on sepsis was studied. Intra-peritoneal injection of LPS 5 mg/kg followed by injection of peptides corresponding to SEQ ID NOs: 3-5, 30 minutes later (as described hereinabove for a dose of 2 mg/kg). Nearly identical results were obtained when the peptides were applied in the sepsis model (FIG. 5B). Interleukin 6 (IL-6) levels were significantly reduced (FIG. 5C) and the mice in the peptide-treated groups appeared healthier, as estimated from their enhanced activity, diminished shivering and less stiff hair, compared to mice treated with LPS alone, *P<0.05, P<0.001, *P<0.0001.

Moreover, assessment of heparanase inhibitory peptides in the inferior vena cava (IVC) thrombosis model, as described in Materials and Methods, was performed with peptides comprising SEQ ID NO: 8, corresponding to SEQ ID NOs: 3-5. The peptides had been injected prior to the procedure, and the results indicate complete inhibition of clot formation without increasing bleeding tendency during the surgery (FIG. 6A; n=5). A large thrombus located distal to the IVC ligation (FIG. 6A, panel I) and after IVC was harvested (FIG. 6A, panel II), was observed. This observation was verified by H&E staining (FIG. 6A, panel III, ×10; FIG. 6A, panel IV, ×100). In subsequent experiments, peptides 3, 4 and 5 were introduced subcutaneously, at a dose of 2 mg/kg, immediately before the IVC exposure. Heparanase was not injected in this line of experiments. Each experimental group included 5 mice. The IVC was re-exposed (FIG. 6A, panel V) and then dissected (FIG. 6A, panel VI). Note that only engorged blood was present and thrombus distal to the IVC ligation was absent. This observation was verified by H&E staining (FIG. 6A, panel VII, ×10; FIG. 6A, panel VIII, ×100). No excess bleeding was observed in the groups treated with peptides as compared to control mice. Images were visualized through a 0.82 MDC objective lens, captured with a Nikon E995 digital camera (Nikon, Tokyo, Japan), and processed with Adobe Photoshop software (Adobe Systems, San Jose, Calif.).

Example 5. The Effect of the Peptides on Tumors In Vivo

Figure 7C:
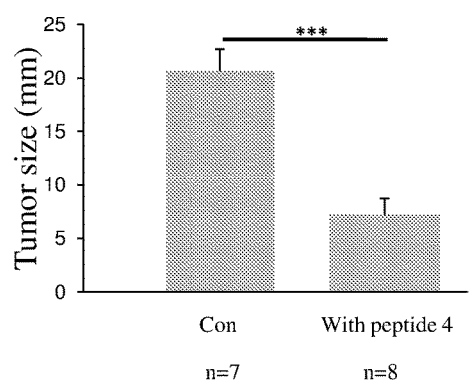
FIG. 7C is a photograph of representative tumors (B16 mouse melanoma) in control mice (upper tumors) and in mice treated with one of the peptides (SEQ ID NO: 4; lower tumors).
Figure 7C:
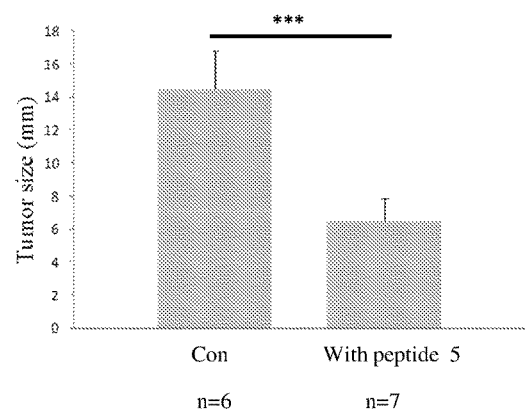
Figure 7C:
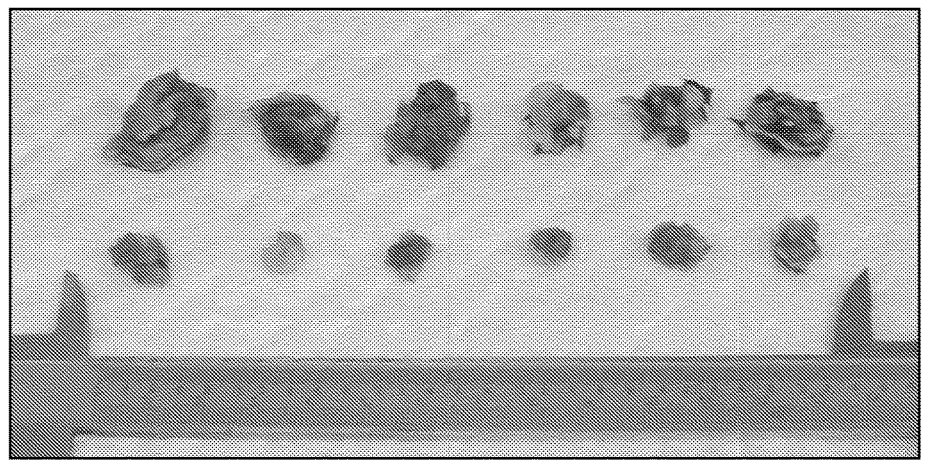
Figure 8A:
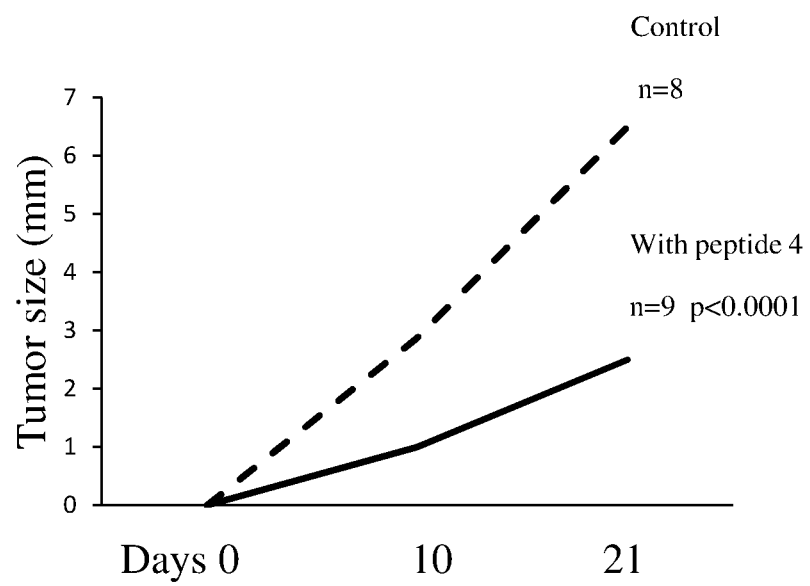
FIG. 8A shows the size of MDA-231 human breast cancer tumors in untreated SKID mice (control, dashed line) and in mice treated with the peptide of SEQ ID NOs: 4 for 21 days, measured at days 0, 10 and 21 of treatment.
Figure 8B:
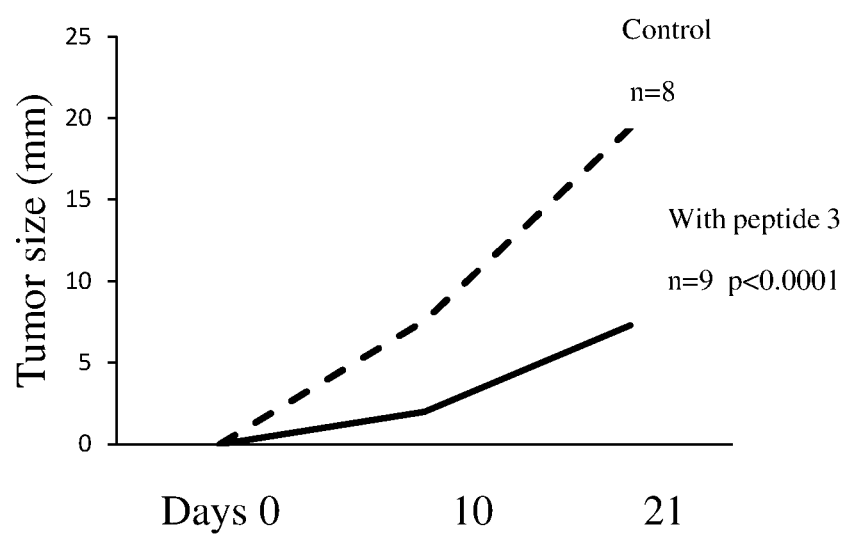
FIG. 8B shows the size of EMT-6 mouse breast cancer tumors in untreated BALB/c mice (control, dashed line) and in mice treated with the peptide of SEQ ID NO: 3 for 21 days, measured at days 0, 10 and 21 of the experiment.

B16 mouse melanoma, EMT-6 mouse breast cancer, and MDA-231 human breast cancer-cell lines were injected subcutaneously to C57BL/6, BALB/c and SKID mice, respectively. Inhibitory peptides of SEQ ID NOs: 3-5 were injected subcutaneously opposite to tumor side, at a dose of 2-4 mg/kg, every other day, starting 4 days after tumor cell injection. Tumor growth was monitored for 3 weeks. Tumors sizes were measured throughout the experiments, where tumor size prior to treatments (day 0) was assigned 0 cm (FIGS. 7A-7B and 8A-8B). Tumor size was significantly (P<0.0001) smaller in mice treated for 3 weeks with any one of the peptides set forth in SEQ ID NOs: 3-5 as compared to control mice (FIGS. 7A-7C). Moreover, the rate of tumor growth in mice treated with the peptides (FIGS. 8A-8B, solid lines) was much lower than the corresponding rate in control mice (FIGS. 8A-8B, dashed line).

Figure 9A:
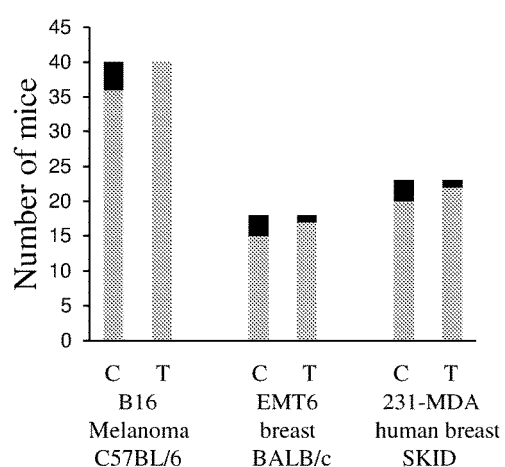
FIG. 9A shows the survival (gray) vs. non-survival (black) of mice bearing B16 mouse melanoma tumors, EMT-6 mouse breast cancer tumors, and MDA-231 human breast cancer tumors, at the end of the 3 weeks control (C; n=82) or treatment (T; n=82) with the peptides of SEQ ID NOs: 3-5,*P<0.05.
Figure 9B:
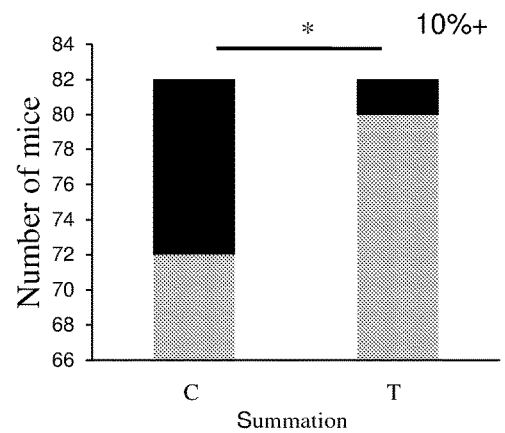
FIG. 9B is a summary of the data showed in FIG. 9A for all mice (n=164) with respect to each experimental group (control and treatment) irrespective of tumor's type.

The effect of inhibitory peptides on the survival rate of tumor-bearing mice was evaluated after 3 weeks of treatment (FIGS. 9A-9B). The result show that 80 out of 82 mice treated with the peptide survived, where only 72 out of 82 control mice survived. This observation corresponds to about 10% improvement in survival of mice treated with the peptides (FIG. 9B).

Figure 10:
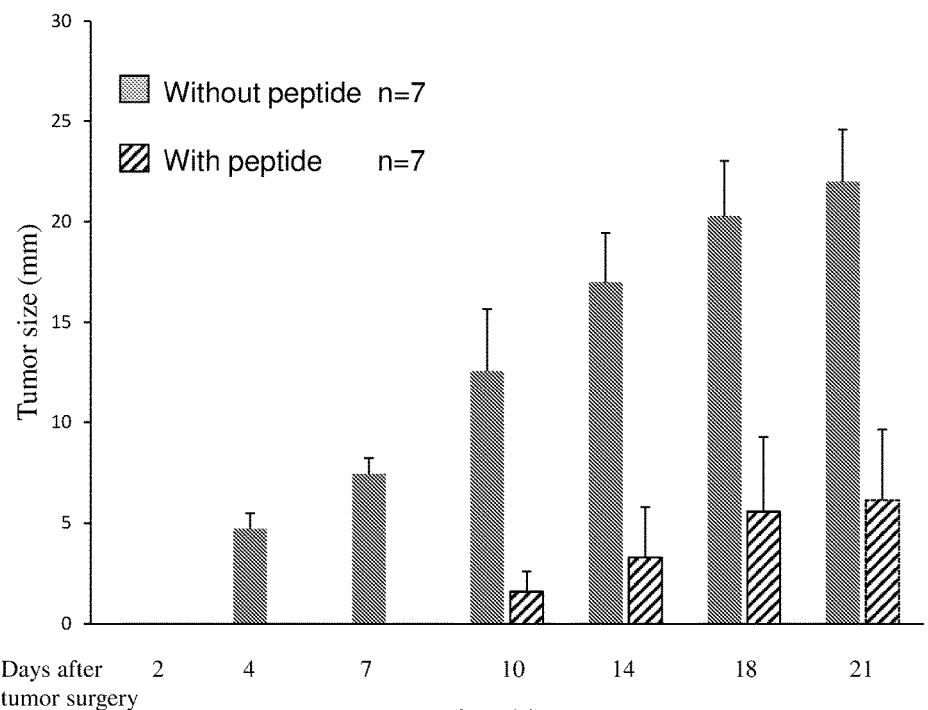
FIG. 10 shows an evaluation of tumor relapse based on the size of secondary B16 mouse melanoma tumors in C57BL/6 mice, as a function of time after removal of the primary tumor, in a control group (gray fill) and in a group of mice treated with the peptide of SEQ ID NO: 4 (dashed fill).

In order to evaluate the effect of the peptides on tumor relapse, tumors were left to grow to a size of about 1-1.5 $cm^3$, and then removed. After tumor removal, the peptides were administered to the treatment group subcutaneously (s.c.) at the opposite flank every other day for 3 weeks. The control group received saline injections subcutaneously every other day for 3 weeks. Tumor, organs, and plasma were studied. As shown in FIG. 10, treatment with the peptides of SEQ ID NOs: 3-5 inhibited tumor for at least one week. After about 10 days, slow increase in tumor size was observed in mice treated with the peptides. However, the resulting tumors were at least 3-fold smaller than the control tumors (P<0.001). At the end of the 3 weeks treatment, 2 of 7 mice in the peptide treated group showed no tumor relapse, while all 7 of the non-treated (control) group developed tumors.

Example 6. The Effect of the Peptides on Tumor Vascularization

Figure 11:
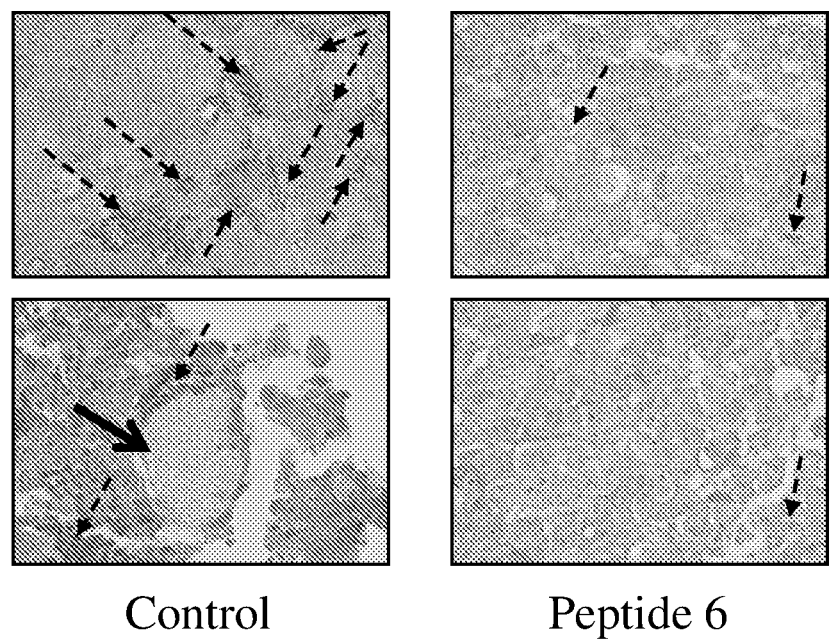
FIG. 11 shows histological sections of B16 mouse melanoma control tumors (left panels) and tumors from mice treated with the peptide corresponding to SEQ ID NO: 4 (right panel), stained with MSB staining, with arrows pointing at vascularization (dashed line arrows) and at a thrombus (solid line arrow).

Treatment with the peptides inhibited, or at least significantly attenuated, tumor vascularization. This activity is shown for example in the MSB stained tumors presented in FIG. 11: control tumor (FIG. 11, left panels) exhibited rich vascularization (dark staining, pointed at by dashed line arrows) and thrombus formation (e.g. FIG. 11, bottom left panel). In contrast, little to null vascularization was found in a tumor treated with the peptide set forth in SEQ ID NO: 4 (FIG. 11, right panels).

Moreover, the peptides did not induce inhibition of tumor cell growth in vitro and had no effect on heparanase enzymatic activity. The results may suggest that the peptides exert their inhibitory effect through inhibition of tumors' vascularization.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating a solid tumor in a subject in need thereof, comprising administering to the subject a therapeutic composition comprising at least one peptide consisting of the amino acid sequence selected from the group consisting of SEQ ID NOs: 8 and 9, thereby treating a solid tumor in a subject in need thereof.

2. The method of claim 1, wherein said treating is attenuating tumor size.

3. The method of claim 1, wherein said solid tumor is a breast cancer tumor.

4. The method of claim 1, wherein said solid tumor is a melanoma tumor.

* * * * *